United States Patent [19]

Jatho et al.

[11] Patent Number: 4,836,031

[45] Date of Patent: Jun. 6, 1989

[54] METHOD AND APPARATUS FOR MEASURING DEFORMATIONS OF TEST SAMPLES IN TESTING MACHINES

[75] Inventors: Ralf Jatho, Seeheim-Jugenheim; Gerhart Hintz, Rossdorf; Guenter Keller, Modautal, all of Fed. Rep. of Germany

[73] Assignee: Carl Schenck AG, Darmstadt, Fed. Rep. of Germany

[21] Appl. No.: 207,729

[22] Filed: Jun. 16, 1988

[30] Foreign Application Priority Data

Nov. 27, 1987 [DE] Fed. Rep. of Germany ....... 3740227

[51] Int. Cl.$^4$ .............................................. G01L 1/24
[52] U.S. Cl. ................................................... 73/800
[58] Field of Search ...................... 73/800; 356/32, 33, 356/34, 35.5, 372, 375, 383; 33/125 A

[56] References Cited

U.S. PATENT DOCUMENTS

| 2,646,716 | 7/1953 | Bowen .................................. 356/32 |
| 3,462,223 | 8/1969 | Tieman et al. ....................... 356/32 |
| 3,592,545 | 7/1971 | Paine et al. ........................... 73/800 |
| 4,181,430 | 1/1980 | Shirota et al. ...................... 356/375 |
| 4,425,043 | 1/1984 | van Rosmalen .................... 356/375 |
| 4,605,857 | 8/1986 | Ninomiya et al. . |

FOREIGN PATENT DOCUMENTS

| 0023643 | 2/1981 | European Pat. Off. . |
| 0194354 | 9/1986 | European Pat. Off. . |
| 0255552 | 2/1988 | European Pat. Off. . |
| 0534151 | 9/1931 | Fed. Rep. of Germany ........ 73/800 |
| 1773642 | 8/1971 | Fed. Rep. of Germany . |
| 2330162 | 12/1974 | Fed. Rep. of Germany . |
| 2602583 | 7/1976 | Fed. Rep. of Germany . |
| 2631663 | 1/1978 | Fed. Rep. of Germany . |
| 3151542 | 7/1983 | Fed. Rep. of Germany . |
| 3346429 | 7/1985 | Fed. Rep. of Germany . |
| 3422988 | 1/1986 | Fed. Rep. of Germany . |
| 0238852 | 8/1969 | U.S.S.R. ............................... 356/32 |
| 895600 | 5/1962 | United Kingdom . |
| 1294234 | 10/1972 | United Kingdom . |

OTHER PUBLICATIONS

Journal of Scientific Instruments (Journal of Physics E), 1969, Series 2, vol. 2, pp. 375-377, Article Entitled: "The Application of a Light-Sensitive Potentiometer in the Measurement of the Mechanical Properties of Single Fibers".

Primary Examiner—John Chapman
Assistant Examiner—Robert R. Raevis
Attorney, Agent, or Firm—W. G. Fasse; D. H. Kane, Jr.

[57] ABSTRACT

In a method and apparatus for measuring deformations of test samples in testing machines, a test sample (4) is clamped into force transmitting units (10, 11). A light source (1) emits a light beam (2) which is reflected from at least one mirror (6, 6') arranged on the force transmitting units (10, 11) to impinge upon a position detector (7) which generates an output signal. The output signal is input to an electronic evaluating circuit (8) to determine the location or rather the location movement of the point of impingement of the light beam on the position detector. Preferably, but not necessarily, each force transmitting unit (10, 11) includes its own mirror (6, 6'), whereby the light beam (2) emitted by the light source (1) is reflected in sequence by the first mirror (6) of the first force transmitting unit (10) onto a second mirror (6') of the second force transmitting unit (11) and then onto the position detector (7). These steps and elements measure a test sample deformation and/or a deformation velocity with a high accuracy and in a simple manner, especially in fast tensile rupture testing machines.

14 Claims, 1 Drawing Sheet

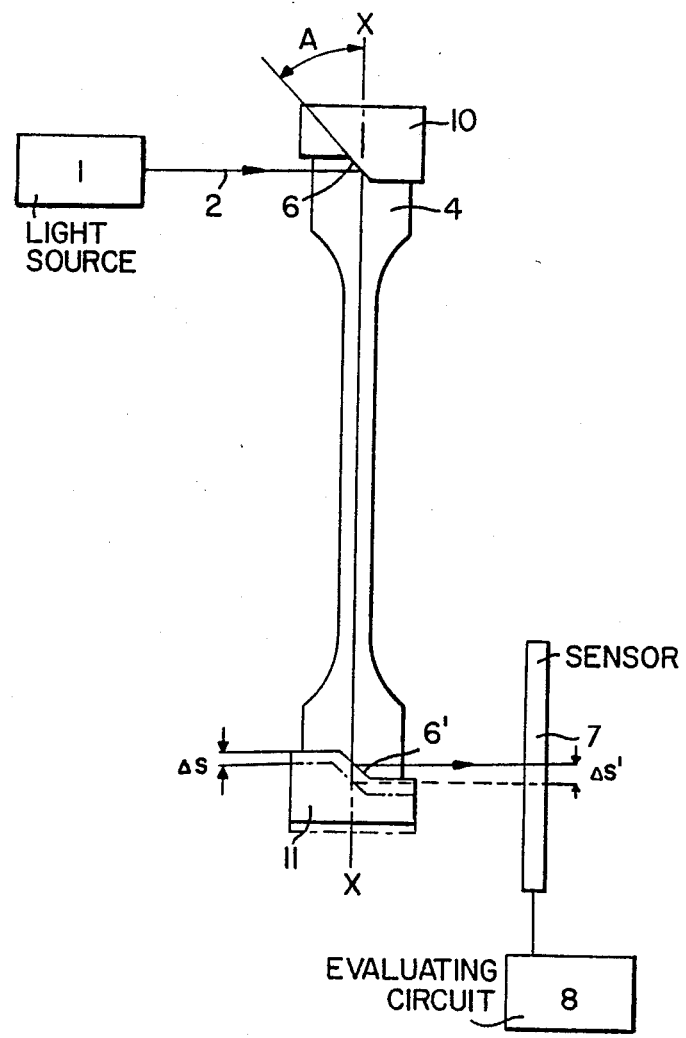

METHOD AND APPARATUS FOR MEASURING DEFORMATIONS OF TEST SAMPLES IN TESTING MACHINES

CROSS-REFERENCE TO RELATED APPLICATIONS

The present application relates to U.S. Ser. No.: 207,754, filed on the same date as the present application, and U.S. Ser. No.: 207,758, also filed concurrently herewith.

FIELD OF THE INVENTION

The invention relates to a method for measuring deformations of test samples in testing machines. The invention further relates to an apparatus for carrying out the present method.

CROSS-REFERENCED APPLICATION

In the above cross-referenced copending application a light source emits a light beam which is reflected from at least one mirror so that the reflected light beam impinges on a position detector. The varying location of the point of light impingement on the detector provides an output signal which is evaluated in an electronic signal processing circuit. The at least one mirror is arranged at an appropriate location on the test sample so as to reflect a light beam onto said position detector or sensor. As the light beam is moving in response to test sample deformations its point of impingement on the position detector or sensor also changes correspondingly and such change is determined and evaluated by said signal processing circuit as a measure of a deformation.

OBJECTS OF THE INVENTION

In view of the foregoing it is the aim of the invention to achieve the following objects singly or in combination:

to expand the possibilities of measuring various kinds of deformations on test samples, more specifically, to effectively measure static and/or dynamic deformations caused in test samples by tensile or compressive forces, as well as deformations caused by twisting or torque moments or bending moments;

to achieve a high accuracy of measuring such deformations even in the micron range;

to effectively measure crack opening or widening in test samples;

to especially achieve accurate measurements for cyclic loading, as well as displacement or distance and velocity measurements in extremely rapidly accelerated test samples, for example for fast tensile rupture testing machines;

to eliminate or compensate the effect of movements of the entire testing machine, for example in the elastic range on measurement results by providing that two mirrors of the arrangement carry out any movements of the entire testing machine; and to provide a simplified arrangement of the light source, mirrors, and position detectors so that the possibility of any angular deviations between the components which would lead to measurement inaccuracies is reduced.

SUMMARY OF THE INVENTION

The above objects have been achieved in a method for measuring deformations of test samples in testing machines according to the invention, wherein the test sample is held or clamped by a first and a second force transmitting unit, whereby each force transmitting unit is provided with a mirror surface. The mirror plane of each mirror surface is arranged at an angle relative to the lengthwise axis of the test sample or the force transmission axis, but parallel to and facing each other. The light beam is reflected in sequence by the mirror arranged on the first force transmitting unit and then by the mirror arranged on the second force transmitting unit to impinge upon a position detector. Preferably, the light beam is initially emitted essentially perpendicularly to the lengthwise force transmission axis, whereby the two mirror planes are oriented at an angle of 45° relative to said lengthwise force transmission direction. The light beam is then reflected by the first mirror to extend essentially parallel to the lengthwise force transmission axis. An arrangement according to the invention provides the necessary components arranged to carry out the above method.

The arrangement for carrying out the above described preferred method embodiment represents an especially simple arrangement which, nonetheless, allows a high accuracy of positioning the components and therewith a high accuracy in the measurement result. A further advantage of avoiding misalignments, reducing the weight of the arrangement, etc., is achieved if the mirrors are formed as mirror surfaces of the force transmitting units themselves. This embodiment is especially advantageous for carrying out such measurements on rapidly accelerated test samples. Since the reflecting or mirror surfaces follow together any absolute movement of the testing machine, such movements are completely compensated and cannot affect the test results.

BRIEF DESCRIPTION OF THE DRAWING

In order that the invention may be clearly understood, it will now be described, by way of example, with reference to the accompanying drawing, wherein the single FIGURE is a schematic front view of the basic arrangement for carrying out the method according to the invention.

DETAILED DESCRIPTION OF PREFERRED EXAMPLE EMBODIMENTS AND OF THE BEST MODE OF THE INVENTION

The test sample 4 under investigation, for example, a flat or round section sample, is clamped into two force transmitting units 10 and 11 of a testing machine, which is not shown in detail since it is conventional. Each force transmitting unit 10 or 11 is essentially a clamping chuck having clamping jaws for holding the test sample 4. These details are not particularly shown. A test force is applied to the test sample 4 by means of the force transmitting units 10 and 11, whereby a deformation occurs in the test sample 4. Such a deformation is determined or measured, using optical means in the method and apparatus of the invention.

A collimated point cross-section light beam 2 is emitted by a light source 1 and directed onto a first mirror surface 6 arranged on the first force transmitting unit 10. This first mirror 6 may, for example, be a mirror surface 6 directly applied on a clamping jaw of the force transmitting unit 10. The mirror surface 6 may, for example, be produced by appropriate machining operations such as grinding and polishing. However, alternatively, the mirror 6 may be a separately formed mirror element 6 which is attached, for example glued, to the force transmitting unit 10.

The light beam 2 is reflected by the mirror 6 and extends parallel to the lengthwise force application axis X—X of the test sample 4, in other words, the force transmission axis. The other end of the test sample 4 is clamped into the second force transmitting unit 11, including a second mirror surface 6'. The light beam extending along the lengthwise axis X—X impinges on the mirror 6', which in turn reflects the light beam 2 toward a position detector or sensor 7. The mirror 6' may be constructed in a manner similar to the mirror 6 described above. The position detector 7 is a typical known opto-electronic position detector such as Model: S1352, manufactured by Hamamatsu Photonics. It is possible to exactly determine the position of the point of impingement of the light beam 2 onto the detector 7 by evaluating an output signal of the detector 7 in a highly accurate electronic evaluating or signal processing circuit 8 of the type MV319 manufactured by C. Schenck AG or in the circuit of FIG. 7 of Dr. Seituer/Hamamatsu pamphlet 26.S . . . 0883.

The first force transmitting unit 10 may be constructed either to remain stationary, or to move during the deformation of the test sample 4. In the first case, the second force transmitting unit 11 would move corresponding to the deformation of the test sample 4, while in the second case the second force transmitting unit 11 would be stationary relative to the testing machine. The example embodiment shown in the FIGURE represents the first case in which the force transmitting unit 10 and the light source 1 are arranged to remain stationary relative to the entire testing machine during the deformation of the test sample 4. Advantageously, the force transmitting unit 10 and the light source 1 may be rigidly attached to a cross-girder member of the testing machine.

In the example embodiment shown in the FIGURE, the light beam 2 emitted by the light source 1 extends orthogonally to the direction defined by the lengthwise axis X—X of the test sample 4 or the force transmission axis. The mirror planes of the mirrors 6 and 6' extend parallel to each other with the mirror surfaces facing each other. The mirror planes extend at an angle A, here for example 45°, relative to the lengthwise axis X—X. The segments of the light beam 2 between the light source 1 and the first mirror 6, between the two mirrors 6 and 6', and finally between the mirror 6' and the position detector 7, all lie in one common plane which is the plane defined by the drawing sheet. The mirrors 6 and 6' are arranged orthogonally to said common plane. Thus, the light source 1 lies on one side of the lengthwise axis X—X while the position detector 7 lies on the other side of the lengthwise axis X—X.

As shown in the FIGURE, for the case of a movable second force transmitting unit, a lengthwise deformation $\Delta s$ of the test sample 4 results in a deviation or movement $\Delta s'$ of the point of impingement of the light beam 2 on the position detector 7. With the arrangement shown, the lengthwise deformation $\Delta s$ is of exactly the same size as the light beam deviation $\Delta s'$. In another embodiment possibility not shown, but described above, the second force transmitting unit 11 remains stationary while the first force transmitting unit 10 moves corresponding to the deformation of the test sample 4. In this case, as the force transmitting unit 10 moves, the light beam reflected by the mirror 6 moves or deviates laterally corresponding to the lengthwise deformation movement of the test sample 4. As a result of the lateral deviation of the reflected light beam, its point of impingement on the second mirror 6' moves, so that a similar deviation $\Delta s'$ is registered on the detector 7. In either case, an electronic evaluating circuit 8 determines and evaluates the light impingement point deviation $\Delta s'$ or movement and thus the corresponding lengthwise deformation $\Delta s$ of the test sample 4. The position detector 7 may be either a one-axis detector for detecting a light point deviation on a line, or a two-axis detector for detecting a light point deviation on a plane. The detector 7, as well as the evaluating circuit 8 may operate either in an analog or a digital manner. By these means deformations or distances in the micron range may be accurately measured in a simple inexpensive way.

As can be seen in the FIGURE, any absolute movement of the testing machine in the vertical direction, or also in the horizontal direction for that matter, that is to say any motion up or down or from side to side of the entire arrangement shown in the FIGURE, does not have an effect on the result of the measurement. This is true because any absolute motions are completely compensated or do not become effective because the test sample 4 and the mirrors 6 and 6', as well as the light source 1 and the detector 7, all carry out any movement of the testing machine. Such an absolute movement would be superimposed on any relative movement carried out by the components during a testing procedure. The compensation is even achieved if the light source 1 and the detector 7 do not follow or carry out the absolute movements of the testing machine, provided the mirrors still receive the light beam. For example, if both mirrors 6 and 6' simultaneously move the same distance in a vertical direction under no-load conditions, while the light source 1 and the position detector 7 remain stationary, then the point of impingement of the light beam 2 onto the position detector 7 will not move. This holds true even if the light source 1 and the position detector 7 are not perfectly stationary, but merely move together in unison.

The example embodiment shown is especially suitable for measuring test sample deformations and/or deformation velocities in fast tensile rupture testing machines. In such machines it has been quite costly and difficult to perform measurements directly on the test sample. The invention solves these problems. The deformations caused in the test sample, as well as the deformation velocity, may be determined by means of the arrangement shown in testing procedures carried out at a high velocity. The position detector and the evaluating circuit are known as such and therefore require no detailed description. It should be mentioned that it is preferred to use digital position detectors in the described arrangement because it is easy to suppress the effects of stray or scattered light in such detectors by electronic means.

Although the invention has been described with reference to specific example embodiments, it will be appreciated, that it is intended to cover all modifications and equivalents within the scope of the appended claims.

What we claim is:

1. A method for measuring deformations of test samples in testing machines, comprising the following steps:
   (a) clamping a test sample into first and second force transmitting means, (b) emitting and directing a light beam onto a first mirror means arranged on said first force transmitting means so that a reflected light beam extends essentially in parallel to a lengthwise axis of said test sample, (c) further reflecting said reflected light beam by second mirror means arranged parallel to said first mirror means on said second force transmitting means for directing a further light beam toward a position detector, (d) receiving said further light beam at a point of light impingement on said position detector for generating an output signal in said position detector dependent on a position change of said point of light impingement, and (e) evaluating said output signal in evaluating circuit means to determine a position change of said point of light impingement representing a measure of a deformation of said test sample.

2. The method of claim 1, wherein said light beam is emitted by light source means in a direction essentially perpendicular to said lengthwise axis, said light beam extending in a plane relative to which planes of said first and second mirror means extend perpendicularly.

3. The method of claim 1, comprising forming said first and second mirror means as integral surfaces on said first and second force transmitting means.

4. The method of claim 1, comprising clamping said test sample at its respective ends into said first and second force transmitting means.

5. The method of claim 1, further comprising generating said emitted light beam as a collimated, point cross-section light beam.

6. The method of claim 1, used for measuring at least one of the following deformation type strain caused deformations, crack opening deformations, and for measuring rapid motion characteristics of test samples.

7. An apparatus for measuring deformations of test samples in testing machines, comprising first and second force transmission means for engaging a test sample, light source means for emitting a light beam, first mirror means arranged in a first mirror plane on said first force transmission means, second mirror means arranged in a second mirror plane on said second force transmission means, whereby said first and second mirror planes extend in parallel to one another and at angle (A) relative to a lengthwise axis of said test sample, said angle (A) being defined between any one of said mirror planes and said lengthwise axis, and further comprising position detector means arranged to receive said light beam at a point of light impingement after said light beam is reflected from said second mirror means, and electronic evaluating circuit means connected to said detector means for determining and evaluating a location movement of said point of light impingement as a measure of said deformations.

8. The apparatus of claim 7, wherein said first and second mirror means respectively comprise a mirror surface forming an integral part of said first and second force transmission means.

9. The apparatus of claim 7, wherein said light source means comprises a laser light source.

10. The apparatus of claim 7, wherein said angle between said lengthwise axis and any of said first and second mirror planes is about 45°, and wherein said light source means emits said light beam perpendicularly to said lengthwise axis and in a plane to which said first and second mirror planes extend perpendicularly.

11. The apparatus of claim 7, wherein said position detector means comprises a one-axis linear detector.

12. The apparatus of claim 7, wherein said position detector means comprises a two-axis planar detector.

13. The apparatus of claim 7, wherein said position detector means comprises an analog position detector.

14. The apparatus of claim 7, wherein said position detector means comprises a digital position detector.

* * * * *